United States Patent [19]

Grimmer et al.

[11] Patent Number: 5,616,737
[45] Date of Patent: Apr. 1, 1997

[54] STEREOSELECTIVE PREPARATION OF (−) 3A,6,6,9A-TETRAMETHYL-PERHYDRO-NAPHTHO[2,1-B]FURAN

[75] Inventors: Johannes Grimmer, Ludwigshafen; Christoph Martin, Mannheim, both of Germany

[73] Assignee: BASF Aktiengesellschaft, Ludwigshafen, Germany

[21] Appl. No.: 674,914

[22] Filed: Jul. 3, 1996

[51] Int. Cl.$^6$ .................................................. C07D 307/92
[52] U.S. Cl. ............................................................. 549/458
[58] Field of Search ............................................. 549/458

[56] References Cited

U.S. PATENT DOCUMENTS

| | | | |
|---|---|---|---|
| 3,029,255 | 4/1962 | Stoll | 549/458 |
| 5,274,134 | 12/1993 | Bruns et al. | 549/458 |

FOREIGN PATENT DOCUMENTS

| | | |
|---|---|---|
| 0204009 | 12/1986 | European Pat. Off. . |
| 3240054 | 5/1984 | Germany . |
| 3912318 | 10/1990 | Germany . |

OTHER PUBLICATIONS

Chemical Abstracts, vol. 105, AN 134193k, 1986.
Helvetica Chimica Acta, vol. 68, pp. 2022–2029, 1985, G. Ohloff, et al., "Significance of the Geminal Dimethyl Group in the Odor Principle of Ambrox".
Dragoco Report, pp. 276–283, 1979, Ernst–Joachim Brunke, "Modifizierte Ambra–Rienchstoffe I. Stereospezifische Synthese Racemischer Analoga Von Ambrox".
Chemical Abstracts, vol. 105, 134193K (1986)–Abstract of Japan, Kokai 61–33184, (1984).

*Primary Examiner*—Bernard Dentz
*Attorney, Agent, or Firm*—Oblon, Spivak, McClelland, Maier & Neustadt, P.C.

[57] ABSTRACT

A process for the stereoselective preparation of (−)3a,6,6,9a-tetramethylperhydronaphtho[2,1-b]furan of the formula Ia

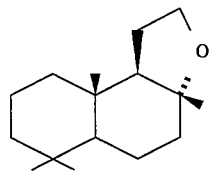

(Ia)

by dehydration and cyclization of decahydro-2-hydroxy-2,5,5,8-tetramethyl-1-naphthaleneethanol using solid acidic catalysts, wherein the decahydro-2-hydroxy-2,5,5,8-tetramethyl-1-naphthaleneethanol is heated in the molten state at from 80° to 200° C. in the presence of from 10 to 100% by weight, based on the diol, of an active acidic aluminum oxide commercially supplied for (preparative) column chromatography.

9 Claims, No Drawings

STEREOSELECTIVE PREPARATION OF (−) 3A,6,6,9A-TETRAMETHYL-PERHYDRO-NAPHTHO[2,1-B]FURAN

The present invention relates to a process for the stereoselective preparation of (−)3a,6,6,9a-tetramethylperhydronaphtho[2,1-b]furan of the formula Ia

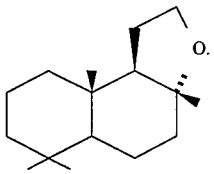
(Ia)

This compound has an amber scent which has been used for decades in perfumery (Ambrox® supplied by Firmenich; Amboxan® supplied by Henkel and Sylvamber® supplied by BASF).

Besides its occurrence in the amber tincture of the sperm whale, this amber scent has now likewise been detected in clary oil (*Salvia sclarea* L.), in labdanum oil (*Cistus tabdaniferus* L.) and in cypress oil (*Cupressus sempervirens* L.) (cf. G. Ohloff in Fragrance Chemistry, Academic Press, 1982, page 543). In perfume compositions it has a desirable amber effect which is effective even at great dilution and, furthermore, ensures excellent fixing even of delicate flowery fragrances. It is mainly used in costly perfume oils. The four diastereomers of this amber scent

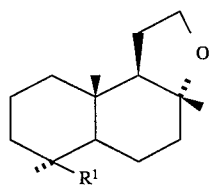
(Ia)

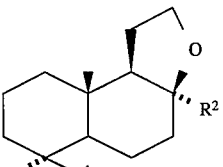
(Ib)

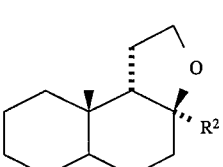
(Ic)

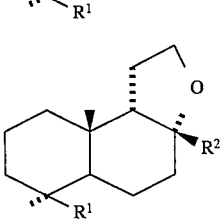
(Id)

Ia–Id differ distinctly from one another. Thus, for example, the odor of "isoambrox" (Ib) is more than one hundred times weaker than that of the compound of the formula Ia (cf. G. Ohloff et al. Helv. Chimica Acta, 68 (1985), 2022–2029), and the odor of "norisoambrox" (formula Ib with $R^1$=H and $R^2$=$CH_3$) is more than 500 times weaker than that of the compound of the formula Ia.

The amber scent of the formula Ia and the diastereomer mixtures of the formulae Ia to Id can be prepared both by partial synthesis from ambrein or diterpenes of the labdane type (eg. sclareol, manool) and by total synthesis (cf. review by E.-J. Brunke, Dragoco-Report. 11/12 (1979), 276 et seq.).

On the industrial scale, the amber scent is mainly prepared by oxidative breakdown (chromic acid, permanganate, ozone) of sclareol, a constituent of the clary concrete. Sclareolide, which is obtained as breakdown product, is converted after reduction with lithium alanate or sodium boranate into a 1,4-diol ("ambroxdiol") which is subsequently cyclized (cf. G. Ohloff, Fortschr. Chem. Forsch. 12/2, (1969) 185 et seq.).

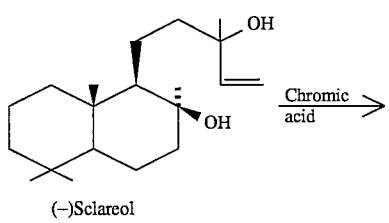
(−)Sclareol

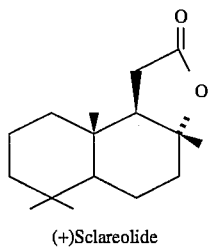
(+)Sclareolide

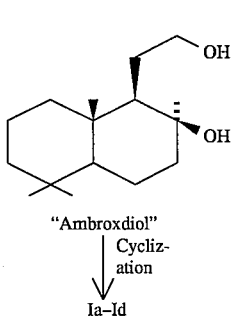
"Ambroxdiol"
| Cyclization
↓
Ia–Id

Because of the fact that, among the four diastereomers, the compound of the formula Ia has the greatest olfactory importance, numerous processes attempting to carry out the last step, the cyclization, stereoselectively have been developed in the past.

Thus, V. E. Sibiertseva et al. described, in Maslo-Zhir, Prom.st., 1979 (12), 25–26, the cyclization of "ambroxdiol" in the presence of p-toluenesulfonic acid. The disadvantage of the process is the dehydration, which cannot be avoided in the acidic medium, of the tertiary hydroxyl group, which leads to losses of selectivity. In addition, the stated yields of 55–60% are unsatisfactory in an industrial process, especially when the costly precursor is taken into account. The use of p-toluenesulfonic acid is also claimed in the processes of Russian Patents SU 345 183 (of 1968), SU 910 561 (of 1980) and SU 529 166 (of 1975).

In the process disclosed in an older patent of Firmenich (DP 860 214 of 1949), naphthalenesulfonic acid (78% yield) and aluminum oxide (50% yield) were described as catalysts. The disadvantages indicated above, such as poor selectivity and unsatisfactory yields, were observed in this case too.

In the process of Spanish Patent 432 815 (of 1976), the cyclization of "ambroxdiol" was carried out with sulfuric acid; the yields obtained in this case were only 29%.

R. C. Cambie et al. described in Aust. J. Chem. 24 (1971), 583–591 and 2365–2377, the cyclization of "ambroxdiol" using p-toluene-sulfonyl chloride in pyridine with 80% yield. The main disadvantages in this case are the use of pyridine, which has an unpleasant odor, with a view to adjusting the quality of the resulting scent, and the relatively long reaction times. In addition, on aqueous workup, pyridine recycling is unavoidable owing to its solubility in water, which leads to an increase in costs.

Cambie used sulfuric acid as catalyst in a second cyclization method. The disadvantages in this case are the long reaction time (>3 days) and the poor yields (43% of theory).

The cyclization process with POCl₃ described by Consortium Elektrochemie in DE-A 3 240 054 (of 1982) was also carried out in anhydrous pyridine, and the disadvantages described above therefore had to be accepted. The yields were only 65% of theory.

P. F. Vead and N. D. Unger described in Synthesis (1983) 816–818, a cyclization method in which trimethylchlorosilane in dimethyl sulfoxide (DMSO) was used as reagent; the yields stated in this case are 85%. As is evident from the experimental example detailed herein, this method represents only a laboratory procedure (mg batches). The use of DMSO is industrially disadvantageous, having to be elaborately recycled after the aqueous workup because of its solubility in water (waste water problems). A crucial disadvantage is furthermore the need to purify the crude amber scent obtained after the reaction to a quality which is acceptable in both chemical and olfactory terms. The chemical purification took place by costly column chromatography, in which case the complete removal of DMSO is usually difficult. Another problem is the frequently difficult industrial handling of trimethylchlorosilane, which is very corrosive and, moreover, toxicologically objectionable.

The same cyclization method is also described in Russian Patent SU 988 817 (of 1980).

Furthermore, EP-A 204 009 discloses a process for preparing Ambrox®, in which sclareol is converted by a biotechnological route into "ambroxdiol", and the latter is cyclized to (−)3a,6,6,9a-tetramethylperhydronaphtho[2,1-b] furan of the formula Ia, The cyclization is carried out using an arylsulfonyl chloride in the presence of acidic compounds such as HCl and acid ion exchangers or in the presence of bases such as pyridine and NaOH. The yields obtained with the cyclization in acidic medium described herein are poor. The disadvantages of cyclization in the presence of organic bases such as pyridine on the industrial scale have been explained above in detail.

Cyclization with sulfonyl chlorides in the presence of alkali metal hydroxides takes place relatively well. However, the disadvantages in this case are the relatively long reaction times, the still inadequate purities of the resulting compound of the formula Ia, and the very high reaction temperature in some cases, which can lead to losses of selectivity.

Furthermore, Chem. Abstr. 105 (1986) 134193 k discloses that on use of white earth, alumina or silica loaded with from 1 to 20% by weight of sulfuric acid, phosphoric acid or polyphosphoric acid as catalysts it is possible to increase the theoretical yields of the compound of the formula Ia to 85–90.5%. The purity of the compound of the formula Ia is reported as 97% and 98% in two examples.

Furthermore, DE 39 12 318 discloses a process for the cyclization of "ambroxdiol" in the presence of acid-loaded aluminas as catalysts, which is characterized by the following features:

1) use of 60–80% by weight of Al₂O₃ based on "ambroxdiol"
2) hydrochloric acid loading from 0.4 to 0.6% by weight
3) apparent density 0.9 g/cm³
4) particle size range from 0.05 to 0.2 mm However, the disadvantages in this case are that the cyclization is not sufficiently stereoselective for olfactory demands, and that very specific alumina catalysts pretreated with hydrochloric acid must be used.

The disadvantage of all the abovementioned processes is the indispensability of solvents, which may have an adverse effect on olfactory assessment, because they are very easily adsorbed by the required product and can be removed only by further costly measures such as steam distillation or prolonged drying times.

It is an object of the present invention to find a highly selective cyclization process which is simple to carry out industrially and which leads to a product with suitable olfactory properties without the disadvantages of the prior art processes.

We have found that this object is achieved by a process for the stereoselective preparation of (−)3a,6,6,9a-tetramethylperhydronaphtho[2,1-b]-furan of the formula Ia

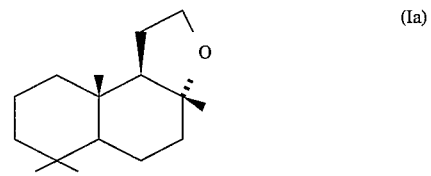

by dehydration and cyclization of decahydro-2-hydroxy-2, 5,5,8-tetramethyl-1-naphthaleneethanol using solid acidic catalysts, wherein the decahydro-2-hydroxy- 2,5,5,8-tetramethyl-1-naphthaleneethanol is heated in the molten state at from 80 to 180° C, preferably 120° to 140° C. in the presence of from 10 to 100% by weight, based on the diol, of an active acidic aluminum oxide commercially supplied for (preparative) column chromatography, for from 1 to 6 hours.

The diol used as starting compound, decahydro-2-hydroxy-2,5,5,8-tetramethyl-1-naphthaleneethanol, is a known compound and can be prepared, for example, by the process of EP-A 204 009.

Suitable as cyclization catalyst is acidic aluminum oxide commercially obtainable for preparative column chromatography, in particular aluminum oxide 90 active, acidic, activity I, for column chromatography supplied by Merck, Darmstadt, the aluminum oxide with the name ICN alumina A, activity 1, supplied by ICN Biomedicals GmbH, or equivalent products of other companies.

The melting point of the starting diol is 133+ C. so that the temperature at the start of the reaction should according to the invention be above this temperature to ensure intensive contact with the catalyst. The melting point of the starting diol is considerably reduced by the (−)3a,6,6,9a-tetramethylperhydronaphtho[2,1-b]furan which forms. Thus, the melting range of the starting diol in the presence of, for example, about 20% of the cyclization product is only about 103°–107° C.

It is therefore advantageous to start the reaction of the diol above its melting point of 133° C. and to allow the temperature slowly to fall to 80° C. during the reaction.

However, it is also possible in principle to start the reaction at temperatures below 133° C. when a certain amount of the cyclization product is added to the reaction mixture at the start. With the addition of about 20% of the cyclization product it is possible to melt the starting mixture at temperatures as low as about 107° C. and to work at these milder temperatures. However, the disadvantage of this is that the required reaction time is doubled at these temperatures.

Temperatures of from 140° C. to about 120° C. are therefore preferably used.

Surprisingly, the required product quality is not adversely affected at these temperatures in the presence of the catalysts described, which is of crucial importance for scents.

The reaction times in the process according to the invention at these temperatures are about 1–6 hours, preferably 2–4 hours.

The reaction rate depends on the reaction temperature so that only very short holdup times are required at very high temperatures, and thus the process according to the invention can also be carried out continuously with negligible losses of selectivity or olfactory quality. The temperatures then used are from 180° to 200° C., preferably 185° to 190° C., with reaction times of from 5 to 20 minutes, preferably 10 to 15 minutes.

After the cyclization reaction is complete, the resulting reaction mixture is either separated from the catalyst by distillation under greatly reduced pressure or dissolved in hot ethanol and the catalyst is removed by filtration.

The product of the formula Ia is isolated from the ethanolic solution by crystallization in a conventional way. Isolation from ethanolic solution is very advantageous because ethanol is anyway used as standard solvent in the perfume industry. The yields are generally greater than 90% of theory with purities of more than 99%.

Another advantage of the process according to the invention is that the catalyst can be regenerated by washing with ethanol and then reused. It is advantageous for the catalyst which results after removal of the ethanolic solution of the reaction mixture and is still at about 70° C. to be washed 1 to 3 times with hot ethanol, and the catalyst can then be reused (cf. Example 3). On reuse, the catalyst can be employed while moist with ethanol, because on heating the reaction mixture under reduced pressure the ethanol distills out even before the elimination of water starts.

It is possible with the process according to the invention to convert decahydro-2-hydroxy-2,5,5,8-tetramethyl-1-naphthalene-ethanol in a very simple but, nevertheless, low-cost and environmentally acceptable manner and in very good yields stereoselectively into (−)3a,6,6,9a-tetramethylperhydronaphtho[2,1-b]furan which is in great demand as fragrance.

EXAMPLE 1

50.8 g (0.2 mol) of ambroxdiol and 25.0 g of aluminum oxide 90 active, acidic, activity I (supplied by Merck) were introduced into a four-neck stirred flask (250 ml) equipped for distillation and, after reducing the pressure to about 30–40 mm Hg with a water pump, the reaction mixture was stirred while slowly heating with a paraffin oil bath to about 140°–145° C. (internal flask temperature). The product began to melt at 133° C. The water formed in the reaction was distilled out. The reaction was complete after 90 minutes (min). The oil bath heating was then switched off, and the mixture was cooled to 75°–80° C. and brought to atmospheric pressure. Then 90 ml of ethanol were added, the reaction mixture was refluxed for 30 min and then cooled to about 50°–55° C., and the catalyst was removed using a G4 glass frit and washed with 60 ml of ethanol. The filtrate was combined with the washing ethanol and the solution was heated to reflux and then water was added dropwise until a marked turbidity appeared at the boiling point, which required about 75–80 ml of water. The mixture was cooled while stirring and, finally, the crystallized product was isolated at 10° C. using a G3 glass frit and was washed with 100 ml of an ethanol/water mixture (2:1) and dried in an oven at 55°–60° C. under about 20 mbar to constant weight. The yield was 43 g (corresponding to 91.4% of theory) with a solidification point of 75°–77° C. The purity of the product was more than 99% according to GC analysis.

EXAMPLE 2

203.2 g (0.8 mol) of ambroxdiol and 100.0 g of aluminum oxide ICN alumina A, activity 1 (supplied by ICN Biomedicals GmbH) were introduced into a 1 liter flask provided with 4 sloping baffles. The flask with the reaction mixture was attached to a rotary evaporator and immersed in an oil bath preheated to 140° C., and the water produced in the reaction was removed by distillation at 24 rpm and 20–24 mm Hg. The reaction was complete after 4.5 hours (h) at 140° C. and 20 mbar. After cooling to about 85° C, the catalyst was removed using a pressure filter preheated to 80° C. and was washed with about 300 ml of ethanol. Filtrate and washing ethanol were combined and heated to reflux. Water was added to the hot clear solution until marked turbidity appeared, which required about 140 ml of water. Slow cooling while stirring resulted in the required product crystallizing out in plate-like crystals. The mass of crystals was kept in a refrigerator at 10° C. overnight and then isolated using a G3 glass frit and washed with an ethanol/water mixture (1:1) and sucked dry. Drying at 55° C. under waterpump vacuum to constant weight resulted in 175 g (corresponding to 92.5% of theory) of a product which was 100% pure according to GC analysis.

Washing of the catalyst while still hot with ethanol returns it to its previous activity so that it can be used several times according to the invention. The catalyst can then be used while moist with ethanol, because on heating of the reaction mixture under reduced pressure the ethanol distils out before the elimination of water starts.

EXAMPLE 3

50.8 g (0.2 mol) of ambroxdiol and 10 g of aluminum oxide 90, acidic (activity I supplied by Merck) were mixed in a 250 ml round-bottomed flask equipped for distillation. While stirring, the mixture was slowly heated under 2.5–3 mbar to 135°–140° C., and the water formed in the reaction was distilled out. After about 30 min, the temperature was increased to 160° C., and the (−)3a,6,6,9a-tetramethylperhydronaphtho[2,1-b]furan was distilled out under 2.5–3 mbar.

The yield was 45.2 g, corresponding to 95.8% of theory. The product was 94% pure according to GC analysis. The melting point was 68°–72° C.

EXAMPLE 4

203.2 g of ambroxdiol were converted as in Example 2 with 100 g of new ICN alumina A, activity 1, and with ICN alumina A, activity 1, which had been regenerated 1 to 3 times by washing the catalyst while still hot with ethanol, under the reaction conditions indicated in the following table, into (−)3a,6,6,9a-tetramethylperhydronaphtho[2,1-b]furan. The yields and purities of the product obtained in each case are indicated in the table.

TABLE

| Example | Catalyst | Reaction temperature [°C.] | Reaction time [h] | Pressure [mbar] | Purity (GC) [%] | Yield [g] | [% of theory] |
|---|---|---|---|---|---|---|---|
| 4a | ICN alumina A, active 1, new | 140 | 3 | 25–20 | 99.9 | 172.0 | 90.95 |
| 4b | regenerated 1x | 138–140 | 4.5 | 20 | 100 | 172.0 | 90.95 |
| 4c | regenerated 2x | 138–140 | 5.0 | 20 | 100 | 172.0 | 90.95 |
| 4d | regenerated 3x | 140 | 5.5 | 22 | 99.95 | 172.0 | 90.95 |

We claim:

1. A process for the stereoselective preparation of (−)3a, 6,6,9a-tetramethylperhydronaphtho[2,1-b]furan of the formula Ia

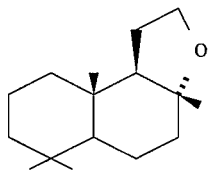

(Ia)

by dehydration and cyclization of decahydro-2-hydroxy-2, 5,5,8-tetramethyl-1-naphthaleneethanol using solid acidic catalysts, wherein the decahydro-2-hydroxy- 2,5,5,8-tetramethyl-1-naphthaleneethanol is heated in the molten state at from 80° to 200° C. in the presence of from 10 to 100% by weight, based on the diol, of an active acidic aluminum oxide commercially supplied for (preparative) column chromatography.

2. A process as claimed in claim 1, wherein the reaction of the molten decahydro-2-hydroxy- 2,5,5,8-tetramethyl-1-naphthaleneethanol is carried out in the presence of aluminum oxide 90 active acidic (activity I) for column chromatography supplied by E. Merck, Darmstadt.

3. A process as claimed in claim 1, wherein the molten decahydro-2-hydroxy-2,5,5,8-tetramethyl-1-naphthaleneethanol is heated in the presence of aluminum oxide with the name ICN Alumina A, act. 1, supplied by ICN Biomedicals GmbH.

4. A process as claimed in claim 1, wherein the reaction of the decahydro-2-hydroxy-2,5,5,8-tetramethyl-1-naphthaleneethanol is started above its melting point of 133° C. and, during the course of the reaction, the temperature is allowed to fall slowly to 80° C.

5. A process as claimed in claim 1, wherein the molten decahydro-2-hydroxy-2,5,5,8-tetramethyl-1-naphthaleneethanol is heated at from 80 to 140° C. for from 1 to 6 hours.

6. A process as claimed in claim 1, wherein the molten decahydro-2-hydroxy-2,5,5,8-tetramethyl-1-naphthaleneethanol is heated at from 180° to 200° C. for from 5 to 20 minutes.

7. A process as claimed in claim 1, wherein the molten decahydro-2-hydroxy-2,5,5,8-tetramethyl-1-naphthaleneethanol is reacted in the presence of aluminum oxide which has been regenerated one or more times by washing with ethanol.

8. A process as claimed in claim 1, wherein the reaction mixture obtained in the reaction is dissolved in hot ethanol, the catalyst is removed and the reaction product is isolated from the ethanolic solution.

9. A process as claimed in claim 1, wherein the reaction mixture obtained in the reaction is separated from the catalyst by distillation under greatly reduced pressure.

* * * * *

UNITED STATES PATENT AND TRADEMARK OFFICE
CERTIFICATE OF CORRECTION

PATENT NO.   : 5,616,737
DATED        : April 1, 1997
INVENTOR(S)  : Johannes GRIMMER, et al.

It is certified that error appears in the above-indentified patent and that said Letters Patent is hereby corrected as shown below:

On the title page, please add after item [22]:

Item [30], Foreign Application Data:

--[30]   Jul. 6, 1995   [DE]   Germany ..... 19524584.9--

Signed and Sealed this

Second Day of December, 1997

Attest:

BRUCE LEHMAN

Attesting Officer

*Commissioner of Patents and Trademarks*